United States Patent [19]

Mori

[11] Patent Number: 5,027,550

[45] Date of Patent: Jul. 2, 1991

[54] APPARATUS FOR CULTIVATING AQUATIC LIVING THINGS IN SEA WATER

[76] Inventor: Kei Mori, 3-16-3-501, Kaminoge, Setagaya-ku, Tokyo, Japan

[21] Appl. No.: 397,701

[22] Filed: Aug. 23, 1989

[30] Foreign Application Priority Data

Oct. 27, 1988 [JP] Japan .............................. 63-271565

[51] Int. Cl.⁵ ...................... A01G 33/00; A01K 61/00
[52] U.S. Cl. ........................................... 47/1.4; 119/3
[58] Field of Search ............... 47/1.4, DIG. 6; 119/3; 126/440, 425, 424; 405/63, 64, 70, 71

[56] References Cited

U.S. PATENT DOCUMENTS 4,699,086 10/1987 Mori ....................................... 119/3
4,699,087 10/1987 Mori ....................................... 119/3
4,703,719 11/1987 Mori ....................................... 47/1.4
4,941,432 7/1990 Ferrari .................................. 119/3

Primary Examiner—James R. Feyrer
Attorney, Agent, or Firm—Jordan and Hamburg

[57] ABSTRACT

Apparatus for cultivating aquatic living things in sea water includes a column vertically installed in water, a solar ray collecting device mounted on the column, a light radiator movably attached to the column and a light guide for transmitting therethrough solar rays from the solar ray collecting device into the light radiator. The radiator is capable of changing its position for radiating aquatic living things such as marine growth or the like according to its increased size due to growth and according to its movement in the sea.

5 Claims, 4 Drawing Sheets

[5,027,550]

APPARATUS FOR CULTIVATING AQUATIC LIVING THINGS IN SEA WATER

BACKGROUND OF THE INVENTION

The present invention relates to an apparatus for cultivating aquatic living things and more specifically for effectively cultivating marine growth such as kelp, sea weed or the like by using solar rays such as solar rays collected and filtered through a solar ray collecting device.

The present applicant has previously proposed to focus the sun's rays or artificial light rays by using lenses or the like, to guide the focused light rays into a fiber optic cable and to transmit the same therethrough to any place where the light is needed for illumination or for other purposes, for example, as a source of light energy for the photosynthesis of plants in order to intensively cultivate them or to cultivate marine growth. The present applicant has also proposed to focus the sun's rays or artificial light rays by using lenses or the like and to guide the focused light rays into a light guide extending into a water tank for cultivating chlorella and then to transmit and radiate the same into the tank.

However, in the case of applying light radiation to marine growth in sea water it is rather difficult to effectively direct the light rays towards the growth which is always oscillating back and forth in the sea. As regards this problem, no solution has heretofore been introduced.

SUMMARY OF THE INVENTION

It is an object of the present invention to provide a marine cultivating apparatus having an underwater light sources that is capable of effectively supplying light rays to marine growth even when it is oscillating i.e. moving back and forth in the sea.

DESCRIPTION OF THE PREFERRED EMBODIMENTS

Figure 1:
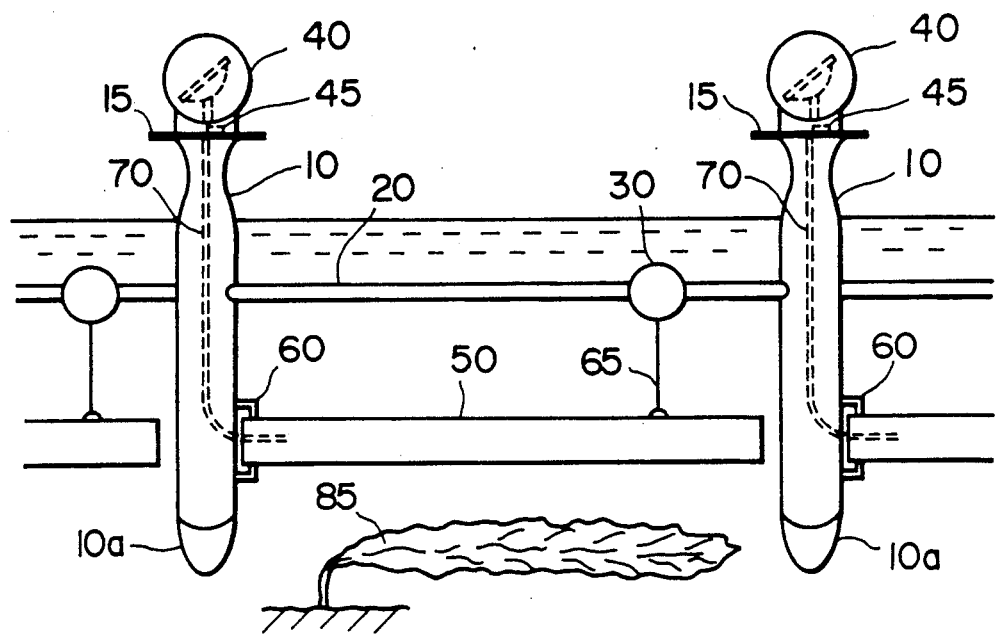
FIG. 1 is a partial construction side view for explaining an embodiment of an apparatus for cultivating aquatic living things in the sea according to the present invention.

FIG. 1 is a partial construction side view for explaining an embodiment of an apparatus for cultivating aquatic living things according to the present invention. In FIG. 1, numeral 10 designates a floating column vertically installed in water (a column may be vertically fixed to the bottom of the sea, however the description hereinafter is concerned with a floating column.) 10a is a weighted element attached to the lower end of the floating column 10, 15 is a water splash guard plate, 20 is a connecting arm for connecting the floating columns, 30 is a knuckle for joining the connecting arms i.e. at the middle portion. 40 is a solar ray collecting device mounted on the floating column 10, 45 is a storage battery or a solar cell i.e. an electric power source for driving a solar ray collecting device and a runner, 50 is a light radiator, 60 is a fixture for fixing the light radiator to the floating column, 65 is a tether made of wire or elastic material 70 is a fiber optic cable laid through the column. As is known, the solar ray collecting device 40 is intended to focus solar rays by means of lenses or the like and to introduce the same into the light-receiving end of a fiber optic cable. The light thus introduced into the fiber optic cable is transmitted therethrough into the light radiator 50 wherein it is used to promote the photosynthesis of marine plants. Furthermore, it is also possible to provide an artificial light source from which artificial light rays are supplied through a separate fiber optic cable to a light radiator in order to radiate marine growth being cultivated in sea water in the case when the natural sunlight is weak or cannot be collected as for example at night. When the light radiator 50 has a transparent external surface, it can emit the light through its whole surface and thereby can more effectively radiate the marine growth. A plurality of floating columns 10 and knuckles 30 used for joining' the connecting arms 20 are connected with each other through the corresponding connecting arms 20. Each light radiator 50 is connected at one end to the corresponding floating column 10 in such a way as to be pivotable on a horizontal plane and hung at the other end by the tether 65 extending from the corresponding knuckle 30. Most of the solar rays collected by the solar ray collecting device 40 and/or the light rays coming from the artificial light source are transmitted through the separate fiber optic cables to each light radiator 50 wherein they are used to promote the photosynthesis of marine plants.

Figure 2:
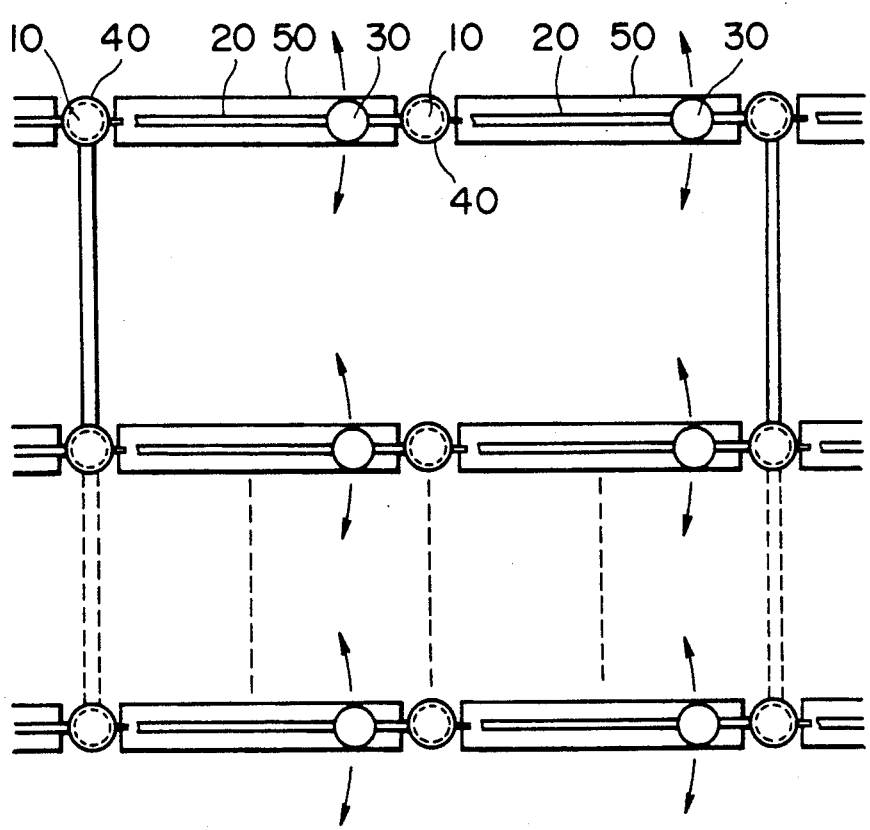
FIG. 2 is a plane view of the apparatus shown in FIG. 1.

FIG. 2 is a plane view of the apparatus shown in FIG. 1. As described above, the light radiator 50, having one of the ends pivotably supported on the floating column 10, can oscillate its other end in the directions indicated by the arrows. Accordingly, as the marine growth being cultivated oscillates in the sea, the light radiator 50 can also oscillate correspondingly in order to direct more effectively the light rays towards the matter to be cultivated.

Figure 3:
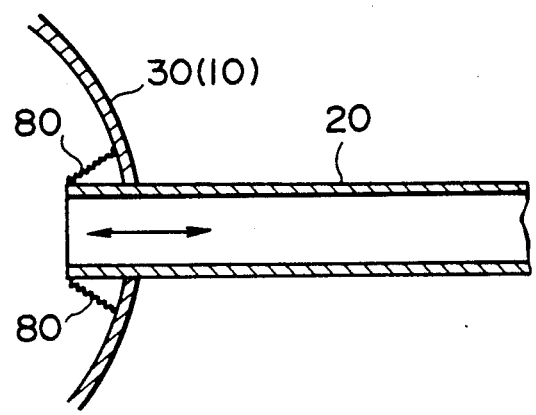
FIG. 3 is a detailed cross-sectional view showing an example of a mechanism for joining a connecting arm with a knuckle used for joining a floating body.

FIG. 3 is a detailed cross-sectional view showing an example of the mechanism used for joining the connecting arm 20 with the knuckle 30 or the floating column 10. In FIG. 3, numeral 80 designates an elastic partition for joining one end of the connecting arm 20 with the knuckle 30 or the floating body 10. Such an elastic connection is effective to absorb the movement of the connecting arm 20 in the directions shown by the arrows at the time of the transversal displacement of the whole assembly.

Figure 4:
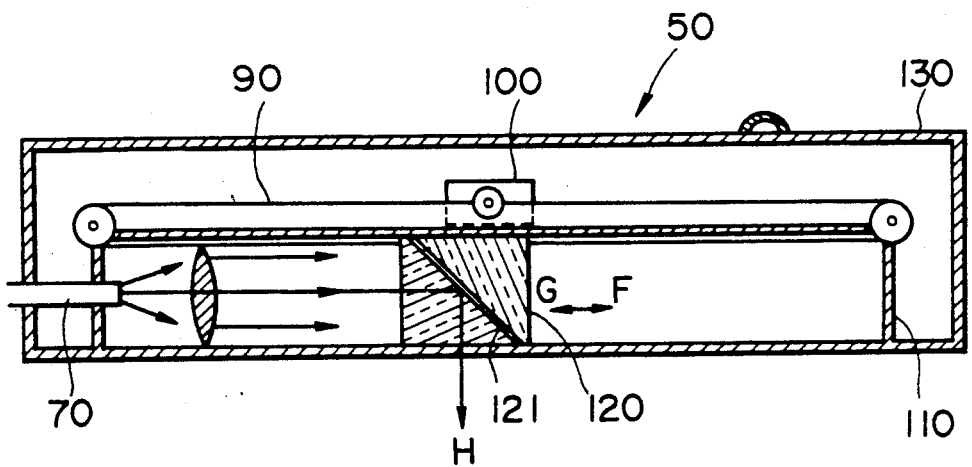
FIG. 4 is a sectional side view for explaining an embodiment of a light radiator to be used in the apparatus according to the present invention.

FIG. 4 is a construction view of the light radiator 20 used in the embodiment of the present invention. In FIG. 4, numeral 110 designates a light guide wherein a runner 120, having a reflecting surface 121 sloping at an angle of about 45°, is installed. The runner 120 can be moved in the directions indicated by the arrows F and G and by means of a wire 90 and a motor 100 which is driven from the electric power source 45 and can reflect the light rays delivered through the fiber optic cable 70 into the light guide 110 so as to emit the same in the direction shown with an arrow H. The reciprocation of the runner 120 in the light radiator makes it possible to radiate the marine growth with the light rays reflected by the reflecting surface 121 at a certain desired time interval. The turning point of the runner's reciprocal movement may vary as the marine growth increases in size due to growth Numeral 130 designates a hermetically sealed container made of a transparent material wherein the light guide 110 and the motor are accommodated.

Figure 5:
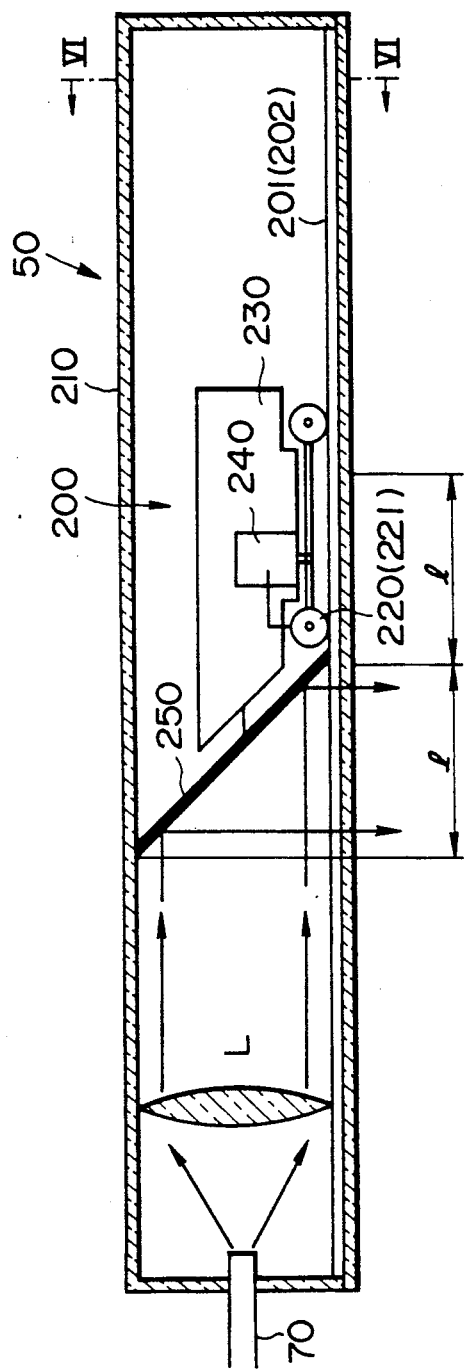
FIG. 5 is a sectional side view showing another embodiment of a light radiator.
Figure 6:
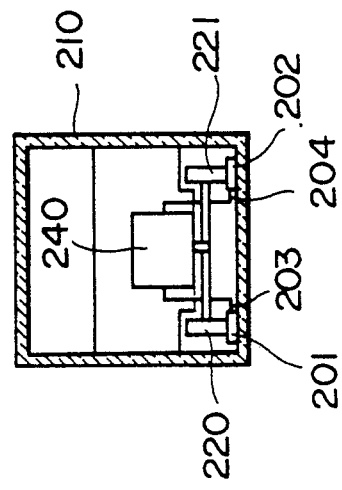
FIG. 6 is a cross-section taken on the line VI—VI shown in FIG. 5.

FIG. 5 is a sectional side view for explaining another example of a light radiator and FIG. 6 is a cross-sectional view taken on line VI—VI of FIG. 5. In FIGS. 5 and 6, 200 is a runner and 210 is a box-shaped body having at least one transparent surface, wherein two rails 201 and 202 are laid in the axial direction thereof and the runner 200 travels on the rails 201 and 201. The runner 200 is constructed of wheels 220 and 221 for travelling on the rails 201 and 202, a body 230 mounted on the wheels, a wheel driving motor 240 mounted on the body 230 and a reflecting plate 250 and so on. Light "L" is introduced from the light-emitting end of a light guide 70 into a box-shaped body 210 wherein it is reflected by a reflecting plate 250 and emitted out of the box's body 210 through the transparent portion. In this embodiment, the rails 201 and 202 are made of a conductive material and sliders 203 and 204 are in contact therewith. When the polarity of the voltage applied between the rails 201 and 202 is changed over, the motor 240 rotates in the reverse direction to reciprocally move the runner 200 inside the box's body 210. In this embodiment, the box 210 has received the light only at one end but it may be also modified to receive the light from both ends and to have one more reflecting plate at the side opposite to the existing reflecting plate 250.

It is also possible to apply a cylindrical body instead of the square box 210 used in the embodiment shown. In the case of a cylindrical body, the rails 201, 202 and the runner body 230 may be installed in the upper portion thereof and a reflecting plate 250 may be held by a supporting arm extending through a slit provided in the body's upper portion in the axial direction thereof. Furthermore, the cylindrical body allows the reflecting plate 250 to be rotated therein while the runner with reflecting plate travels therein, thereby creating a wider light radiation. In this case, the light can be evenly radiated all around the cylinder's body, if the runner moves stepwise by the distance "l" corresponding to the length of the projection line to the moving axis of the reflecting sloped plate and the reflecting sloped plate rotates at each stopped position of the runner.

Figure 7:
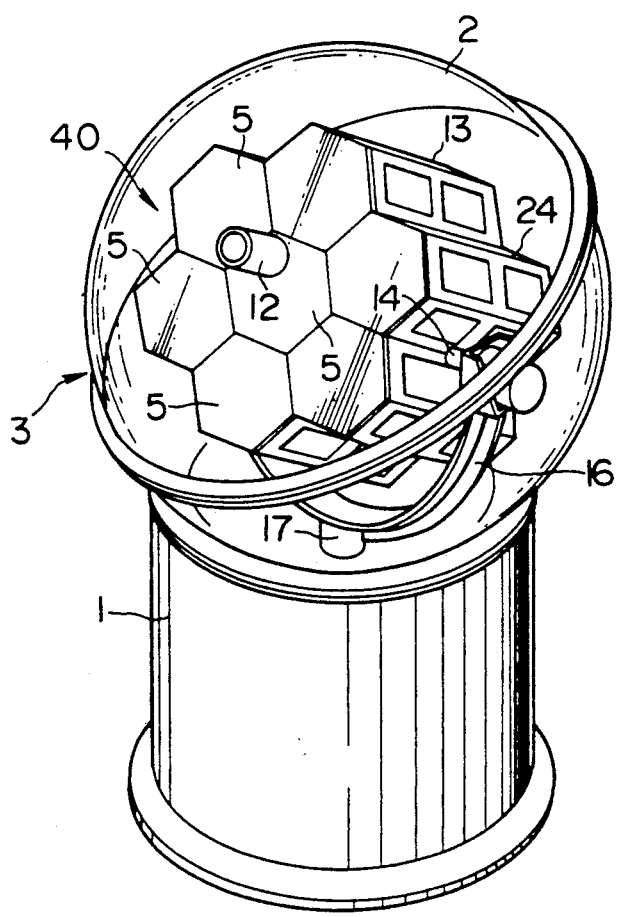
FIG. 7 is a perspective view of a solar ray collecting device used in the embodiment of the present invention.

FIG. 7 is a perspective view illustrating, by way of example, a solar ray collecting device 40. In FIG. 7, a capsule 3 for use in the solar ray collecting device is constructed in the shape of a cylindrical body 1 and a transparent dome-shaped head 2. As shown in FIG. 7, the solar ray collecting device 40 is accommodated in the capsule while the device is being used. The solar ray collecting device 40 comprises one lens, several lenses or possibly a large number of lenses (for example, 7 or 19 lenses) 5, a solar position sensor 12 for detecting the sun's location, a support frame body 13 for integrally holding the lens 11 and sensor 12, a first-revolution shaft 14 for rotating the support frame 13, a rotating, first revolution shaft 14, a support arm 16 for rotatably supporting said revolving shaft 14 and a second-revolving shaft 17 for rotating said support arm 16 around an axis perpendicularly intersecting the first revolving shaft 14. The direction of the sun is detected by mean of the solar position sensor 12 and its detection signal controls the first and second revolution shafts so as to always direct the lens 5 toward the sun, and the sunlight focused by the lens 5 is guided into the fiber optic cable 70 through its light-receiving end-surface set at the focal point of the lens. The guided sunlight is transmitted through the fiber optic cable 70 into the light radiator 50.

As is apparent from the foregoing description, according to the present invention, since each light radiator can oscillate i.e. move back and forth in the sea at the same time as the marine growth oscillates, the light rays coming from said radiators are always directed towards the marine growth being cultivated and thereby the efficiency of their growth may be improved. Furthermore, a runner can reciprocate each light radiator and the turning point of its travel can also be adjusted as the marine growth increases in size. This will assure the increased efficiency of the cultivation of the marine growth.

I claim:

1. An apparatus for providing supplemental light during cultivating of aquatic living things in sea water, comprising at least one column in the water, means for maintaining said column in vertical attitude, the improvement comprising a light radiator movably attached to the column, means pivotally mounting said radiator to said column to allow aid radiator to be capable of changing its position for radiating aquatic living things such as kelp of the like according to the movement in the sea water current and a means communicating the solar ray collecting device and the light radiator for transmitting solar rays from the solar ray collecting device into the water adjacent said light radiator.

2. An apparatus for supplemental lighting in the cultivation of aquatic living things in sea water according to claim 1, further characterized in that a plurality of columns are associated by means of connecting arms.

3. An apparatus for supplemental lighting in the cultivation of aquatic living things in sea water according to claim 1, further characterized in that the light radiator comprises a container having a transparent external walls for transmitting the light rays to be used for growing said kelp or the like.

4. An apparatus for supplemental lighting in the cultivation of aquatic living things in sea water according to claim 2, further characterized in that at least one knuckle for joining the connecting arms is provided.

5. An apparatus for supplemental lighting in the cultivating of aquatic living things in sea water according to claim 4, further characterized in that the light radiator has two ends and includes attachment means at a first end, said attachment means being attached intermediate the ends of the column by means so as to be pivotal on a horizontal plane, a second end, said second end including a tether comprising a wire connected to the at least one knuckle.

* * * * *